(12) United States Patent
Tietjen et al.

(10) Patent No.: US 6,479,043 B1
(45) Date of Patent: Nov. 12, 2002

(54) DEPILATORY COMPOSITION

(75) Inventors: Marlene Tietjen, New York, NY (US); Marie Luciano, East Islip, NY (US)

(73) Assignee: Del Laboratories, Inc., Farmingdale, NY (US)

( * ) Notice: Subject to any disclaimer, the term of this patent is extended or adjusted under 35 U.S.C. 154(b) by 0 days.

(21) Appl. No.: 09/678,924

(22) Filed: Oct. 4, 2000

(51) Int. Cl.⁷ .......................... A61K 7/06; A61K 7/155; A61K 7/15

(52) U.S. Cl. .................. 424/73; 424/70.1; 424/70.5

(58) Field of Search ..................... 424/73, 70.1, 70.5

(56) References Cited

U.S. PATENT DOCUMENTS 5,725,847 A * 3/1998 De La Mettrie et al. .. 424/70.1

* cited by examiner

*Primary Examiner*—James M. Spear
(74) *Attorney, Agent, or Firm*—Kirschstein, et al.

(57) ABSTRACT

A depilatory composition comprising a topically acceptable lotion, gel or cream vehicle, a thioglycolate or thiol depilating agent, and about 0.1 to about 20.0% by weight of solid particles of non-expanded polyethylene, jojoba wax, carnauba wax or candelilla wax. Preferred vehicles include about 50–85% by weight of deionized water. The compositions optionally may include emollierits, skin conditioners, buffering agents, viscosity increasing agents, emulsion stabilizers such as stearyl and cetearyl alcohol, pH adjusters, chelating agents, fragrance, color, lubricants, propellants or biological agents.

17 Claims, No Drawings

DEPILATORY COMPOSITION

BACKGROUND OF THE INVENTION

1. Field of the Invention

The present invention relates to a composition useful in the removal of human body hair and methods for utilizing the same.

2. Description of the Prior Art

Since time immemorial, people have sought to remove unwanted hair from the body for cosmetic, medical, social and other reasons. The most primitive and probably the earliest methods devised for removing such unwanted hair were mechanical in nature, e.g., grasping a single hair or a group of hairs by their ends and forcibly plucking them out of the skin by their roots, or effecting the same operation by use of tweezers or other mechanical grasping devices. Shaving and abrasion of the skin by use of a razor or a knife or any abrasive has also been practiced for millenia as a method for hair removal.

Many centuries ago it was discovered that certain naturally occurring chemical substances, such as certain plant extracts, had the ability to cause the removal of human body hair when applied to a particular skin surface. Many of these naturally occurring chemical depilatories, however were quite harsh, causing substantial irritation to human skin, particularly to sensitive skin areas such as the face, and were frequently malodorous as well.

In modern times, several new depilatory agents and methods have been developed. Electrolysis, whereby a fine wire is inserted into each individual hair follicle and a mild electric current is sent through the wire to destroy the hair-forming cell at the base of the follicle, is a widely-utilized technique for cosmetic hair removal. In addition, X-ray techniques have been used whereby a brief exposure of a skin area to a relatively mild dosage of radiation caused the hair in that area to fall out.

Probably the most widely used depilatory agents developed in modem times are commercially-sold creams and ointments which contain as their active ingredient disulfide bond breakers such as salts of mercaptan acids, particularly salts of thioglycolic acid. These salts attack the most recently formed portion of the hair shaft, that is, the part closest to the skin surface. They act by rupturing the disulfide bonds in the keratin protein found in the hair shaft, weakening the hair and causing it to be ruptured at the surface of the skin, an effect somewhat similar to closely shaving the skin area. The hair root, however, remains in the follicle and the disulfide bond breaking salts have a deleterious effect on the skin and give rise to unpleasant odors.

Another cosmetic hair removal technique currently practiced in the art, primarily by cosmeticians and other professionals, involves the application of flowable wax to a hairy area. The wax is allowed to cool and harden, whereupon it enmeshes the hair which it contacts. The hardened wax then is stripped from the skin, pulling out the enmeshed hair by its roots. New hairs generally will not appear at the skin surface for a period of weeks.

In the medical sphere, hair removal is frequently an important part of pre-surgical preparation. To the present day, the almost universally practiced method for removing the hair from the area where an operation is to be performed is to shave the area with a razor and a suitable lubricated or cream. Because even the closest shave leaves a small amount of stubble, and because hair growth reappears fairly quickly after shaving, the shaving procedure is normally performed almost immediately before the patient is brought into the operating room. Although more efficient and long-lasting hair removal methods are available, such as the use of chemical depilatories or flowable waxes described above, such techniques are disfavored for pre-surgical use because of their tendency to cause irritation of the skin area which can lead to possible infection and other unwanted complications.

More recently, attempts have been made to formulate hair removal products comprising sticky semi-liquid compositions from unrefined sugar, said compositions to be used by applying them to the hairy area and then pressing paper or similar material against the area and pulling away the hair enmeshed by the sticky composition. Such compositions were initially not commercially feasible, however, because unrefined sugar is expensive and not widely available for commercial use in this country and there is some technical difficulty in making suitable homogeneous formulations of unrefined sugar on a commercial scale. Commercial products have been produced containing corn syrup as the tack-imparting component, however, as disclosed, e.g., in U.S. Pat. No. 4,842,610.

In U.S. Pat. No. 5,725,847 there is disclosed a hair-removing composition comprising a cosmetically acceptable medium in which there is dispersed a structuring agent, insoluble in that medium and formed of solid particles, which imparts a deformable solid appearance to the composition in which the medium is contained. The solid "structuring agent" is capable of being removed from the skin using a diluent and is composed preferably of expanded copolymer particles of acrylonitrile and an acrylic and/or styrene and/or vinylidene chloride monomer, hollow glass beads or nylon particles. The solid particles are characterized as imparting improved texture and removability to the depilatory composition, which otherwise comprises standard hair-softening agents such as thioglycolates and auxiliary cosmetic ingredients. The particles are from 1 to 300 $\mu$m in diameter, preferably from 10–100 $\mu$m. U.S. Pat. No. 5,725,847 teaches, however, that particles of corn starch, pyrogenous silica or non-expanded polyester, polyurethane or polyethylene cannot be used to obtain a solid composition which is removed well from the skin during rinsing.

SUMMARY OF THE INVENTION

1. Objects of the Invention

It is an object of the present invention to provide compositions for use in the removal of human hair that are safe, effective, non-irritating and non-toxic and that can be utilized in simple and inexpensive hair-removal methods.

An additional object of the present invention is to provide compositions as described above which enhance the wetting of the hair to be removed.

A further object of the present invention is to provide compositions as described above in the form of lotions, gels or creams.

Still another object of the invention is to provide compositions as described above which contains particles or beads that enhance the wetting of body hair and facilitate removal when rinsing off the composition together with the digested hair.

2. Brief Description of the Invention

In keeping with these objects and others which will become apparent hereinafter, the present invention resides, briefly stated, in a hair-removing composition in the form of a lotion, gel or cream comprising a depilating agent, e.g., a thiol or thioglycolate compound, and about 0.1 to about 20% by weight of particles or beads composed of a polyethylene material or of a wax such as jojoba, carnauba or candelilla.

Optionally, the depilatory compositions of the present invention can include additives such as emollients, skin conditioners, buffering agents, viscosity increasing agents or thickeners and other conventional ingredients known in the art for incorporation into topically applied medicated and non-medicated lotions, gels and creams.

In use, the composition of the invention is applied to a hairy area of the human body which it is desired to depilate and then removed after a suitable period of time, for example by rinsing with water.

DETAILED DESCRIPTION OF THE INVENTION

The depilatory composition of the present invention differs from prior art depilatories containing solid particles such as beads or pellets. Whereas the prior art compositions were in the form of deformable solids and contained only particles comprising hollow glass beads, expanded thermoplastic resin particles and the like, the present composition in the form of a lotion, gel or cream and contains as its solid or pellet phase only natural wax beads or non-expanded polyethylene pellets, particularly pellets of polyethylene homopolymers. The particles of these materials provide significantly better abrasiveness, yielding more efficient lifting of the hair to be removed to allow complete and rapid wetting, and also are more easily washed off with water than the prior art compositions containing glass or resin beads. Furthermore, the natural wax beads or pellets of the instant composition are safe to use, non-toxic, easy to incorporate into a variety of mild cosmetic formulations and relatively inexpensive.

The composition of the invention comprises (a) a topically acceptable lotion, gel or cream vehicle, (b) about 2.0 to about 10.0 % by weight of at least one depilating (i.e., hair digesting or decomposing) agent, and (c) about 0.1 to about 20% by weight, and preferably about 0.1 to about 10% by weight, of particles or beads composed of a polyethylene material or of a wax or wax ester (referred to hereinafter, collectively, as "wax") such as jojoba, carnauba or candelilla. In a most preferred embodiment, the composition comprises about 0.1 to about 5.0% by weight of the polyethylene or wax particles.

The solid particles, beads or pellets in the composition are sized at about 20 to about 400 mesh, preferably about 30 to about 200 mesh and most preferably about 30 to about 100 mesh.

Preferred vehicles contain about 50 to about 85% by weight of deionized water alone or deionized water containing or mixed with other cosmetically acceptable solvents in which the components of the composition are soluble or miscible. Preferred depilating agents include sodium thioglycolate, calcium thioglycolate and potassium thioglycolate. More than one of these thioglycolates may be present in the composition.

The novel composition may optionally include a variety of conventional additives and adjunct ingredients commonly used in the art of formulating topically applied compositions. These optional ingredients may include, but are not limited to, emollients and skin conditioners such as mineral oil, sesame oil, vitamin E oil, chamomile oil, jojoba oil, avocado oil, squalane and glycerine; buffering agents such as sodium silicate; viscosity increasing agents such as acrylate or methacrylate copolymers; emulsion stabilizers such as stearyl and cetearyl alcohol and mixtures containing the same; pH adjusters such as sodium or calcium hydroxide; chelating agents or preservatives such as tetrasodium EDTA; and: biological additives such as aloe vera gel. Fragrance, color, lubricants, propellants and other additives may be utilized as deemed necessary in accordance with conventional practices in the cosmetics and toiletries industries.

To remove unwanted hair from a particular body area, the depilatory composition of the invention is applied to the skin surface of the hairy area to form a coating. After waiting for a sufficient period of time for the active depilatory ingredient to "digest" or break down the hair shafts, typically 5–15 minutes, the composition is rinsed off the skin thoroughly with water.

The composition of the invention is highly effective as a depilatory because of its ability to rapidly lift and thoroughly saturate each hair shaft. Moreover, the materials for producing the composition are readily available and can be inexpensively mixed on a commercial scale with ease and little technical sophistication.

The following are illustrative examples of a hair removal composition in accordance with the present invention. These examples are not intended, however, to limit or restrict the scope of the invention in any way and should not be construed as identifying specific materials, parameters or ranges which must be utilized exclusively in order to practice the present invention.

EXAMPLES 1–3

Depilatoly Lotions

Three different depilatory lotion compositions were produced using the ingredients set forth below in Table I, each ingredient being present in the compositions in the percentage by weight specified in the Table.

TABLE I

| Ingredients | CTFA Name | % (w/w) Ex. 1 | Ex. 2 | Ex. 3 |
|---|---|---|---|---|
| Deionized water | Water | 74.25 | 73.95 | 73.45 |
| Sodium Silicate | Sodium Silicate | 3.00 | 3.00 | 3.00 |
| Calcium Hydroxide | Calcium Hydroxide | 5.00 | 5.00 | 5.00 |
| Calcium Thioglycolate | Calcium Thioglycolate | 5.00 | 5.00 | 5.00 |
| STRUCTURE ™ 3001 (Nat. Starch and Chem. Co., Bridgewater, NJ) | Acrylates/Ceteth-20 Itaconate Copolymer | 0.60 | 0.60 | 0.60 |
| Mineral Oil | Mineral Oil | 6.00 | 6.00 | 6.00 |
| HETOXOL J ™ (Bernel Chemical, Englewood, NJ) | Cetearyl Alcohol, Ceteareth-20 | 4.00 | 4.00 | 4.00 |
| Stearyl Alcohol | Stearyl Alcohol | 1.25 | 1.25 | 1.25 |
| FITODERM ™ (Centerchem, Inc., Stamford, CT) | Squalane | 0.10 | 0.10 | 0.10 |
| Sesame Oil | Sesame Oil | 0.10 | 0.10 | 0.10 |
| Vitamin E Oil | Tocopheryl Acetate | 0.10 | 0.10 | 0.10 |
| Herbal Aloe Frag 495C3 | Fragrance | 0.40 | 0.40 | 0.40 |
| Jojoba BioBeads ™ (Int'l Sourcing, Inc., Saddle River, NJ) | Jojoba esters, hydrogenated jojoba oil | 0.20 | 0.50 | 1.00 |

EXAMPLES 4–6

Depilatory Lotions with Aloe

Three different depilatory lotion compositions with Aloe were produced using the ingredients set forth below in Table II, each ingredient being present in the compositions in the percentage by weight specified in the Table.

TABLE II

| Ingredients | CTFA Name | % (w/w) Ex. 4 | Ex. 5 | Ex. 6 |
|---|---|---|---|---|
| Deionized water | Water | 80.50 | 80.00 | 79.50 |
| Sodium Silicate | Sodium Silicate | 3.00 | 3.00 | 3.00 |
| Calcium Hydroxide | Calcium Hydroxide | 5.00 | 5.00 | 5.00 |
| Calcium Thioglycolate | Calcium Thioglycolate | 4.00 | 4.00 | 4.00 |
| ROBANE ™ (Robeco, Inc., New York, NY) | Squalane | 0.10 | 0.10 | 0.10 |
| BLANDOL ™ (Witco Chemica., New York, NY) | Mineral Oil | 2.00 | 2.00 | 2.00 |
| HETOXOL J ™ | Cetearyl Alcohol, Ceteareth-20 | 3.00 | 3.00 | 3.00 |
| Stearyl Alcohol | Stearyl Alcohol | 1.00 | 1.00 | 1.00 |
| Vitamin E Oil | Tocopheryl Acetate | 0.10 | 0.10 | 0.10 |
| Avocado Oil | Avocado Oil | 0.10 | 0.10 | 0.10 |
| Jojoba Oil | Jojoba Oil | 0.10 | 0.10 | 0.10 |
| Chamomile Oil | Chamomile Oil | 0.10 | 0.10 | 0.10 |
| Aloe Vera Lipoquinone ™ (Thorne Research, Sandpoint, Idaho) | Aloe Extract | 0.10 | 0.10 | 0.10 |
| Polyethylene 617A (polyethylene homopolymers, Allied Signal, Morristown, NJ) | | 0.50 | 1.00 | 1.50 |
| Herbal Aloe Frag 495C3 | Fragrance | 0.40 | 0.40 | 0.40 |

EXAMPLE 7

Depilatory Gel

A depilatory gel composition was produced using the ingredients set forth below in Table III, each ingredient being present in the compositions in the percentage by weight specified in the Table.

TABLE III

| Ingredients | CTFA Name | % (w/w) Ex. 7 |
|---|---|---|
| Deionized Water | Water | 73.70 |
| Aculyn ™ 22 (Rohm and Haas, Philadelphia, PA) | Acrylates/Steareth-20, Methacrylate Copolymer | 6.00 |
| Sodium Hydroxide | Sodium Hydroxide | 2.50 |
| Hampene ™ Na₄ (Hampshire Chemical, Lexington, MA) | Tetrasodium Hydroxide | 0.10 |
| Sodium Silicate | Sodium Silicate | 1.00 |
| Sodium Thioglycolate | Sodium Thioglycolate | 6.00 |
| Potassium Thioglycolate | Potassium Thioglycolate | 3.50 |
| Calcium Thioglycolate | Calcium Thioglycolate | 0.50 |
| Glycerin 96% | Glycerin | 6.00 |
| Aloe Vera Gel | Aloe Vera Gel | 0.10 |
| Fragrance #16989 | Fragrance | 0.50 |
| Jojoba BioBeads ™ | Jojoba esters, hydrogenated jojoba oil | 0.10 |

It will thus be seen that there is provided compositions which achieve the various objects of the invention and where are well adapted to meet the conditions of practical use.

As various possible embodiments might be made of the above invention and as various changes might be made in the embodiments above set forth, it is to be understood that all matter herein described is to be interpreted as illustrative and not in a limiting sense.

What is claimed as new and desired to be protected by letters patent is set forth in the appended claims:

We claim:

1. A depilatory composition comprising:
   a. a topically acceptable lotion, gel or cream vehicle;
   b. about 2.0 to about 10.0% by weight of at least one depilating agent selected from the group consisting of thioglycolate and thiol compounds; and
   c. about 0.1 to about 10.0% by weight of solid particles of non-expanded polyethylene, jojoba wax, carnauba wax or candelilla wax.

2. A depilatory composition according to claim 1 wherein said vehicle contains about 50 to about 85% by weight of deionized water.

3. A depilatory composition according to claim 1 which additionally comprises aloe vera gel.

4. A depilatory composition according to claim 1 which comprises solid particles of jojoba wax.

5. A depilatory composition according to claim 1 wherein said depilating agent is a thioglycolate selected from the group consisting of sodium thioglycolate, calcium thioglycolate and potassium thioglycolate.

6. A depilatory composition according to claim 1 which comprises solid particles of non-expanded polyethylene homopolymers.

7. A depilatory composition according to claim 1 which comprises about 0.1 to about 5.0% by weight of said solid particles.

8. A depilatory composition according to claim 1 wherein said solid particles are sized at about 20 to about 400 mesh.

9. A depilatory composition according to claim 8 wherein said solid particles are sized at about 30 to about 200 mesh.

10. A depilatory composition according to claim 9 wherein said solid particles are sized at about 30 to about 100 mesh.

11. A depilatory composition according to claim 1 which additionally comprises emollients, skin conditioners, buffering agents, viscosity increasing agents, emulsion stabilizers, pH adjusters, chelating agents, fragrance, color, lubricants or propellants.

12. A depilatory composition according to claim 11 wherein said emollients and skin conditioners are selected from the group consisting of mineral oil, sesame oil, vitamin E oil, chamomile oil, jojoba oil, avocado oil, squalane and glycerine.

13. A depilatory composition according to claim 11 wherein said pH adjusters are selected from the group consisting of calcium hiydroxide and sodium hydroxide.

14. A depilatory composition according to claim 1 in the form of a lotion comprising by weight about 73–75% deionized water, about 5% of at least one thioglycolate depilating agent and about 0.2–1.0% of jojoba wax particles.

15. A depilatory composition according to claim 1 in the form of a lotion comprising by weight about 97–81% deionized water, about 4% of at least one thioglycolate depilating agent and about 0.5–1.5% of polyethylene homopolymer particles.

16. A depilatory composition according to claim 15 which additionally comprises aloe vera gel.

17. A depilatory composition according to claim 1 in the form of a gel comprising by weight about 73–75% deionized water, about 9–10% of at least one thioglycolate depilating agent and about 0.1% of jojoba wax particles.

* * * * *